(12) United States Patent
Collins et al.

(10) Patent No.: US 11,976,921 B2
(45) Date of Patent: May 7, 2024

(54) METHOD AND APPARATUS FOR REDUCING MAGNETIC TRACKING ERROR DUE TO FLOOR DISTORTION

(71) Applicant: PENUMBRA, INC., Alameda, CA (US)

(72) Inventors: Michael D. Collins, Fremont, CA (US); Alejandro S. Diaz, Ross, CA (US); Oded Y. Zur, Kochav Yair (IL); Cameron J. Mahon, Guelph (CA); Branislav Vasilijevic, Oakville (CA); Amir Rubin, Los Gatos, CA (US)

(73) Assignee: Penumbra, Inc., Alameda, CA (US)

( * ) Notice: Subject to any disclaimer, the term of this patent is extended or adjusted under 35 U.S.C. 154(b) by 0 days.

(21) Appl. No.: 17/834,173

(22) Filed: Jun. 7, 2022

(65) Prior Publication Data
US 2023/0083524 A1    Mar. 16, 2023

Related U.S. Application Data

(60) Provisional application No. 63/277,752, filed on Nov. 10, 2021, provisional application No. 63/245,141, filed on Sep. 16, 2021.

(51) Int. Cl.
*G01R 33/025* (2006.01)
*G01B 7/00* (2006.01)

(52) U.S. Cl.
CPC ........... *G01B 7/003* (2013.01); *G01R 33/025* (2013.01)

(58) Field of Classification Search
None
See application file for complete search history.

(56) References Cited

U.S. PATENT DOCUMENTS

| | | |
|---|---|---|
| 4,737,794 A | 4/1988 | Jones |
| 6,073,043 A | 6/2000 | Schneider |
| 6,528,989 B1 * | 3/2003 | Hansen ............... G01D 5/2046 324/207.17 |
| 2008/0125997 A1 * | 5/2008 | Li ........................ A61B 90/39 702/94 |
| 2008/0162074 A1 * | 7/2008 | Schneider ............. A61B 34/20 702/150 |
| 2019/0353745 A1 * | 11/2019 | Zur ...................... G01S 17/875 |

(Continued)

*Primary Examiner* — Jermele M Hollington
*Assistant Examiner* — Suresh K Rajaputra
(74) *Attorney, Agent, or Firm* — Haley Guiliano LLP (57) ABSTRACT

A method and apparatus for reducing magnetic tracking error in the position and orientation determined in a magnetic tracking system having a magnetic field generator. In some embodiments, the measured position and orientation of a sensor is compared to an expected theoretical position and orientation. Any error is assumed to be from "floor distortion," i.e., eddy currents in the floor caused by the magnetic field generated by the magnetic field transmitter. The floor distortion is modeled as being caused by eddy currents caused by a second magnetic field transmitter that is a reflection of the actual transmitter. An algorithm iteratively searches over a parameter space to minimize the difference between the measured position and orientation and the theoretical position and orientation, and applies a correction to the measured position and orientation. The measurements and corrections of the position and orientation run in real-time with no additional hardware or calibration required.

9 Claims, 4 Drawing Sheets

(56) References Cited

U.S. PATENT DOCUMENTS

| | | |
|---|---|---|
| 2020/0133405 A1 | 4/2020 | Chan |
| 2020/0158487 A1* | 5/2020 | Zur .................... G01R 33/028 |
| 2020/0319267 A1* | 10/2020 | Ashe .................... A61B 34/20 |
| 2021/0386485 A1* | 12/2021 | Schneider ............. A61B 5/062 |

* cited by examiner

METHOD AND APPARATUS FOR REDUCING MAGNETIC TRACKING ERROR DUE TO FLOOR DISTORTION

This application claims priority to Provisional Application No. 63/245,141, filed Sep. 16, 2021, and Provisional Application No. 63/277,752, filed Nov. 10, 2021, which are incorporated by reference herein in their entireties.

FIELD OF THE INVENTION

The present invention relates generally to magnetic tracking devices, and more particularly to the reduction of magnetic tracking error due to distortion of the magnetic field in such devices.

BACKGROUND OF THE INVENTION

Alternating current (AC) magnetic tracking systems typically use a method in which magnetic fields are generated and measured using a system of orthogonal coils to generate position and orientation information which is used by a computer system. One common application is tracking a user for the purpose of playing a video game or being immersed in a virtual reality world.

In some prior art systems, a transmitter has three orthogonal coils that generate the magnetic field signal, and may be located in a fixed position, such as in a local base station, video game console or other apparatus. A receiver, also known as a sensor, in a tracking device similarly has three orthogonal magnetic field sensing coils, and provides information about the sensed magnetic field to a processor, which derives the position and orientation of the tracking device relative to the base station from such information.

Such AC electromagnetic trackers, and the processors that determine the position and orientation of such trackers, are well known to those of skill in the art. One such example, U.S. Pat. No. 4,737,794 ("the '794 patent"), teaches a "method and apparatus for determining remote object orientation and position with an electromagnetic coupling." It shows a transmitter comprising a plurality of radiating antennas, located at a source to provide a plurality of magnetic fields spanning three dimensional space and defining a source reference coordinate frame, and a receiver comprising a plurality of receiving antennas located on an object to be tracked for receiving that field. A processor receives the outputs from the receiving antennas and converts the received components of the transmitted magnetic fields into remote object position and orientation relative to the source reference coordinate frame. The antennas may be, for example, dipole antennas, loop antennas, or coil antennas. The terms "antennas" and "coils" are used interchangeably herein.

In some prior art embodiments, a transmitter may be located in a fixed position, such as in a local base station, video game console or other apparatus. A receiver in a tracking device provides information about the sensed magnetic fields to a processor, which derives the position and orientation of the tracking device relative to the base station from such information. In some embodiments, the transmitter and receiver are "synchronized" to ensure that the receiver correctly determines the phases of the magnetic fields generated by the transmitter.

There are a number of factors that limit the accuracy of such magnetic tracking systems. The strength of the magnetic fields between a tracking device and a base station transmitter suffers from attenuation over distance, which decreases accuracy in the detection of the magnetic fields by the tracker. Conducting surfaces in the environment may cause distortion in the magnetic fields, particularly if those objects contain conducting materials, as they may contain eddy currents induced by the generated magnetic fields that in turn generate secondary magnetic fields that interfere with the ability of a receiver to accurately detect the source magnetic fields.

Distortion in a magnetic tracking system may have a variety of causes; one significant cause of distortion in such a system is "floor distortion," i.e., the distortion from eddy currents in conducting materials in the floor (such as rebar) that are caused by the magnetic field provided by the magnetic field from the transmitter in the tracking system. (While there can also possibly be eddy currents in the ceiling and walls, floor distortion is so named because the primary effect is generally eddy currents in the floor.)

Floor distortion can result in errors in the position and orientation determined by a magnetic tracking system. In extreme cases, the transmitter and receiver may be unable to synchronize the phases of the magnetic fields as above, or, having been synchronized, may subsequently desynchronize if the distortion is severe.

Some prior art attempts to reduce floor distortion use additional hardware, and thus involve additional expense, require calibration at each site, or involve complicated algorithms that necessitate significant computing resources and thus take time to arrive at a solution.

It is desirable to be able to create a magnetic tracking system that can dynamically correct for floor distortion without additional hardware or calibration, and require as little computing resources as possible.

SUMMARY OF THE INVENTION

A system and method is disclosed which reduces magnetic tracking error caused by floor distortion in the position and orientation determined by a magnetic tracking system.

One embodiment discloses a system for reducing magnetic tracking error in a determined position and orientation of a receiver in an electromagnetic tracking system, comprising: a transmitter having a plurality of source magnetic coils configured to generate a magnetic field; a receiver having a plurality of sensor magnetic coils configured to sense the magnetic field and generate magnetic sensor data; and a processor configured to: determine that there is error due to distortion of the magnetic field in the determined position and orientation of the receiver relative to the transmitter as represented by a first signal matrix created using the magnetic sensor data from the sensor magnetic coils; determine that the error due to distortion of the magnetic field in the determined position and orientation of the receiver represented by the first signal matrix exceeds a predetermined threshold; model the distortion of the magnetic field as a result of eddy currents in a floor under the transmitter; determine from the model of the distortion of the magnetic field a correction factor to compensate for the error in the position and orientation of the receiver represented by the first signal matrix; compute a second signal matrix by applying the first correction factor to the first signal matrix; and determine a corrected position and orientation of the receiver from the second signal matrix.

Another embodiment discloses a method of reducing magnetic tracking error in a determined position and orientation of a receiver in an electromagnetic tracking system, comprising: generating a magnetic field from a plurality of source magnetic coils in a transmitter; generating magnetic sensor data by sensing the magnetic field using a plurality of sensor magnetic coils in a receiver; and determining, by a processor, that there is error due to distortion of the magnetic field in the determined position and orientation of the receiver relative to the transmitter as represented by a first signal matrix created using the magnetic sensor data from the sensor magnetic coils; determining, by the processor, that the error due to distortion in the magnetic field in the determined position and orientation of the receiver represented by the first signal matrix exceeds a predetermined threshold; modeling, by the processor, the distortion of the magnetic field as a result of eddy currents in a floor under the transmitter; determining, by the processor, from the model of the distortion of the magnetic field a correction factor to compensate for the error in the position and orientation of the receiver represented by the first signal matrix; and computing, by the processor, a second signal matrix by applying the first correction factor to the first signal matrix; and determining, by the processor, a corrected position and orientation of the receiver from the second signal matrix.

Still another embodiment discloses a non-transitory computer readable storage medium having embodied thereon instructions for causing a computing device to execute a method of reducing magnetic tracking error in a determined position and orientation of a receiver in an electromagnetic tracking system, the method comprising: generating a magnetic field from a plurality of source magnetic coils in a transmitter; generating magnetic sensor data by sensing the magnetic field using a plurality of sensor magnetic coils in a receiver; and determining, by a processor, that there is error due to distortion of the magnetic field in the determined position and orientation of the receiver relative to the transmitter as represented by a first signal matrix created using the magnetic sensor data from the sensor magnetic coils; determining, by the processor, that the error due to distortion of the magnetic field in the determined position and orientation of the receiver represented by the first signal matrix exceeds a predetermined threshold; modeling, by the processor, the distortion of the magnetic field as a result of eddy currents in a floor under the transmitter; determining, by the processor, from the model of the distortion of the magnetic field a correction factor to compensate for the error in the position and orientation of the receiver represented by the first signal matrix; and computing, by the processor, a second signal matrix by applying the first correction factor to the first signal matrix; and determining, by the processor, a corrected position and orientation of the receiver from the second signal matrix.

DETAILED DESCRIPTION OF THE INVENTION

A system and method is disclosed which reduces magnetic tracking error due to floor distortion of the magnetic field in the position and orientation determined by use of a magnetic tracking system. In the present approach, any distortion is assumed to be "floor distortion," i.e., eddy currents in the floor caused by the magnetic field generated by the magnetic field transmitter, rather than more general types of distortion.

In some embodiments, the measured position and orientation of a receiver is compared to an expected theoretical position and orientation. Any error must be modeled in order to correct for the error; in the present approach, any error is assumed to be from floor distortion, and modeled as being caused by eddy currents in a wire loop in the floor caused by a second magnetic field transmitter that is a reflection of the actual transmitter along a vertical axis relative to the floor, i.e., to the earth's gravity. An algorithm uses the model of the distortion to determine a correction factor by iteratively searching over a parameter space to minimize the difference between the measured position and orientation and the theoretical position and orientation, and applies the determined correction factor to the measured position and orientation to obtain a more accurate actual position and orientation.

Test results have shown that by modeling floor distortion this way, the present approach generally results in better error correction for floor distortion than some prior art methods and is particularly useful with sensors located closer to the floor such as those on a user's lower limbs (e.g., feet, ankles, knees, etc.) because, due to their proximity to the floor, those sensors are more affected by floor distortion. Further, in the present approach the measurements of the position and orientation run in real-time, and no additional hardware or calibration is required. The system and method described herein may thus be quickly and easily applied to detect and reduce error in the determination of position and orientation of a receiver due to floor distortion.

In some embodiments, the tracking system includes a magnetic tracking system having a transmitter and one or more receivers, and inertial measurement units (IMUs), typically containing at least an accelerometer and gyroscope, attached to both the transmitter and the receiver(s). In some embodiments, the transmitter and receivers may communicate with a processor wirelessly, while in other embodiments there may be wired connections.

As above, there have been prior art efforts to reduce the effects of distortion of the magnetic field in determining the position and orientation of a receiver. Some of these have required additional hardware, such as optical cameras, or calibration for particular environments.

Other prior art efforts have involved attempting to subtract out all of the parts of a measurement that do not conform to an ideal generated magnetic field. One such effort may be seen in U.S. patent publication application no. 2019/0353745 ("the '745 application"), commonly owned by the applicant of the present application and entitled "Method and Apparatus for Reducing Magnetic Tracking Error." In the '745 publication, gravity information is obtained from an inertial measurement unit ("IMU") and used to minimize the effect of distortion by removing parts of a measurement that differ from an ideal magnetic field.

In the present approach, by contrast, the distortion is not considered to be general distortion as in the '745 publication, but rather is assumed to be floor distortion. A more specific model of the distortion is used in which the eddy currents in the floor are assumed to due to a horizontal wire loop in the floor that is affected by a second magnetic field source that is a reflection of the actual field source along a vertical axis relative to the floor, i.e., a theoretical second magnetic field source under the floor.

In some embodiments, the amount of detected error due to distortion of the electromagnetic field is first measured. If the error due to distortion is under a predetermined threshold, the uncorrected position and orientation determined by the tracking system (the "standard solution") may be taken to be the correct position and orientation. If error due to the electromagnetic field distortion above the threshold is detected, a correction algorithm that models the distortion as floor distortion may be used.

In an electromagnetic tracking system the three magnetic fields are sensed and separated to generate a signal that is a 3×3 signal matrix, called "SigMat" herein, which represents a total of nine measures of the three transmitted magnetic fields; each column corresponds to the sensed field from a separate one of the three coils of the transmitter, and each row corresponds to a separate one of the three coils of the receiver. One example of a 3×3 matrix that might represent SigMat is:

| a11 | a12 | a13 |
| a21 | a22 | a23 |
| a31 | a32 | a33 | where a11 through a33 represent the nine measures of the three magnetic fields, one measure of each magnetic field by each of the three receiver coils. It is the evaluation of SigMat that results in a determination of the position and orientation of the receiver.

Determining a SigMat from a particular position and orientation of the receiver is straightforward using the formula for the electromagnetic fields. A transmitter "TX" generates, in good approximation, three simple dipole fields. One of skill in the art will appreciate that it is relatively straightforward to predict the SigMat values from a particular position and orientation by using the formula for dipole fields. The inverse problem, i.e., determining the position and orientation of the receiver from a SigMat, is usually harder, but in the case of three dipole fields generated by orthogonal coils can also be solved analytically. In other cases, iterative methods (e.g., successive approximations) are usually used, and such iterative methods may also be used in the case of orthogonal fields as well.

Figure 1:
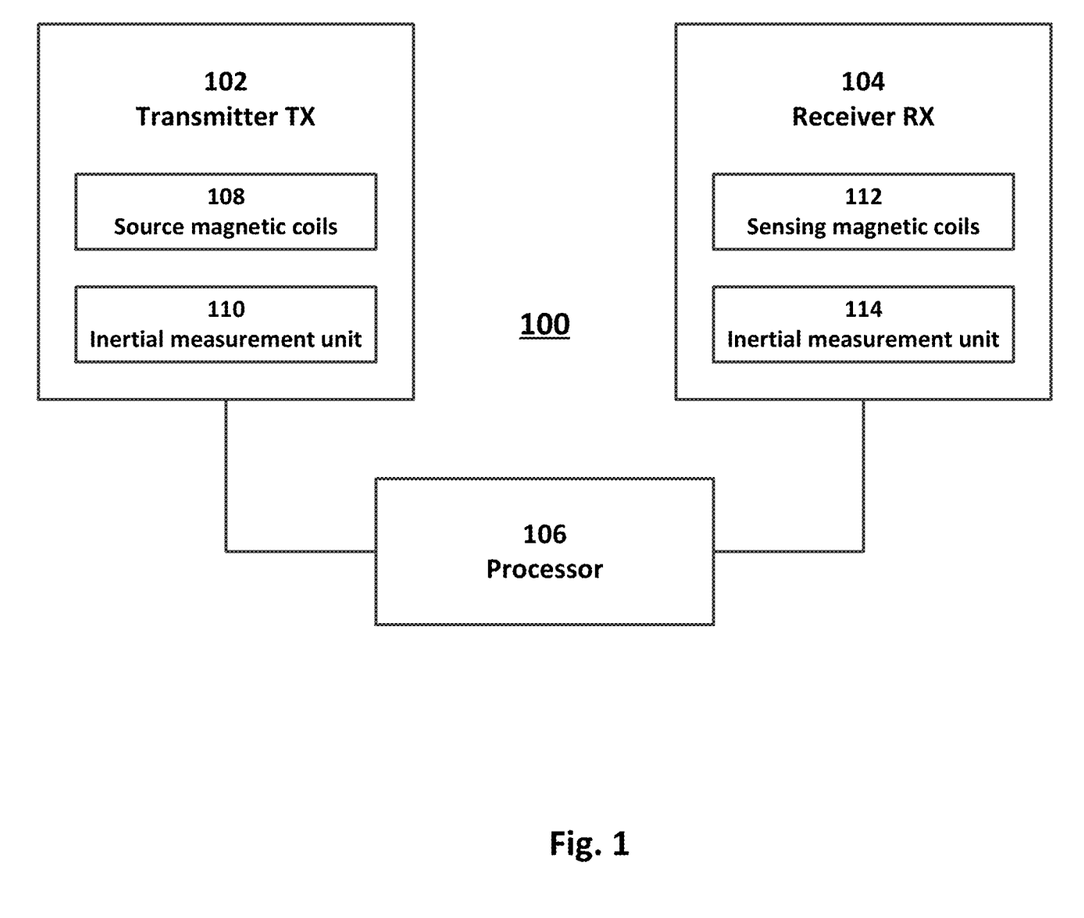
FIG. 1 is a block diagram of a system for reducing magnetic tracking error due to distortion of the magnetic field in a magnetic tracking system according to one embodiment of the present approach.

FIG. 1 is a block diagram of a system for reducing magnetic tracking error due to distortion of the magnetic field in a magnetic tracking system according to one embodiment of the present approach. System 100 contains a transmitter TX 102, a receiver RX 104 and a processor 106; in some embodiments there may be multiple receivers 104. As above, transmitter 102 may be located in a base station, or, in some embodiments, on a user's body, such as on the back, while receiver 104 is attached to some movable object or person. Also as above, transmitter 102 contains source magnetic coils 108 for generating magnetic fields, while receiver 104 contains sensing magnetic coils 112 for sensing the magnetic fields. In the present embodiment, transmitter 102 and receiver 104 each contain an IMU 110 and 114, respectively; IMUs 110 and 114 each have a known physical offset from the respective source magnetic coils and sensing magnetic coils.

System 100 also contains processor 106, which generates a SigMat and performs error reduction as described herein from the data it receives from transmitter 102 and receiver 104, and then generates a position and orientation of the receiver. As above, the transmitter 102 and receiver 104 may communicate with processor 106 wirelessly, or may use a wired connection to do so. In some embodiments processor 106 may be part of a receiver, or there may be multiple processors, each performing a different function; for example, one processor may calculate the SigMat, while another processor may perform the distortion correction described herein.

To reduce the distortion error, the processor first evaluates the SigMat that is generated from sensing coil data. In one embodiment, the model that is used to generate a SigMat when not correcting for distortion is:

$$X(r,\theta)=R(\theta)'*B(r)*R_{tx} \quad \text{(Equation 1)}$$

where:
  $X(r, \theta)$ is the 3×3 SigMat matrix (as sensed in receiver coordinates) for a position and orientation $(r, \theta)$;
  $R(\theta)$ is the rotation matrix expressed by the quaternion parameter $\theta$;
  $R_{tx}$ is the rotation matrix of the transmitter, as found from another source, usually an IMU orientation filter;
  $B(r)$ is the function that defines the SigMat at a position r in the transmitter's reference frame, i.e., an expression of the 3 magnetic fields at position r as the columns of a 3×3 matrix (in transmitter coordinates).

(In the present approach, it is not necessary to obtain a gravity vector from the IMUs as in the '745 publication discussed above, but rather the IMUs are used only to obtain orientation of the transmitter and receiver(s) and for synchronization here. One of skill in the art will appreciate that the IMU orientation information is a superset to the gravity vector, i.e., the gravity vector can be easily deduced from the IMU information.)

In this embodiment, a solver algorithm is used to search for the parameters that produce the smallest difference between the measured SigMat and the expected SigMat, to find a function F such that:

$$F(x)=X_{meas}-X(x) \quad \text{(Equation 2)}$$

where:
  x is the vector of parameters being solved for, i.e., the position and orientation of the receiver;
  $X_{meas}$ is the real SigMat measured as computed by the processor;
  $X(x)$ is the SigMat model specifying the expected SigMat for parameters x.

The algorithm iteratively searches over the parameter space x to find the specific parameter vector $\hat{x}$ that minimizes the value of $F(x)$. The set of parameters that are the components of $\hat{x}$ contain the solution for the position and orientation of the receiver.

As is known in the art, when distortion is present, the minimum value of $F(x)$ found in this way may not be accurate. In some approaches, limiting the number of unknown parameters in x will limit the exposure to false local minima of $F(x)$ and thus improve the accuracy of the model.

However, a more accurate model of the SigMat requires more parameters. In the approach of the '745 publication, an additional parameter P is defined to account for any distortion, where P is the set of three values specifying the strength of each frequency of the magnetic field from the eddy currents in the floor as they are received by the receiver's sensor.

In this prior approach, this results in an equation for the SigMat:

$$X(r,y,P)=R(y)'*(B(r)+G_{rx}*P)*R_{tx} \quad \text{(Equation 3)}$$

where:
- r is the position vector of the sensor in the transmitter reference frame;
- B(r) constitutes the primary Sigmat;
- y is the yaw orientation component of the rotation θ, while pitch and roll are obtained from the IMU gravity vector and constrained as constants within the model;
- $R_{tx}$ is the rotation matrix obtained from the transmitter IMU;
- $G_{rx}$ is a gravity column vector obtained from the sensor IMU;
- R(y) is the rotation matrix as defined by the constant sensor IMU pitch and roll and the given yaw parameter y;
- P is a size-3 row vector expressing the intensity of the 3 frequencies in the Eddy currents.

One of skill in the art will appreciate that the quaternion parameter θ expresses the full 3D rotation; however, because pitch and roll are often kept fixed, the notation is sometimes used incorrectly so that functions of θ may effectively become functions of the yaw y.

One of skill in the art will appreciate that there are now seven parameters to be solved for. As detailed in the '745 publication, an algorithm iteratively optimizes the seven parameters in this equation to find a value of x=[r, yaw, P}' that results in a minimum value of F(x) as above. The position and orientation found this way will account for distortion, including any floor distortion to at least some degree, and thus will be more accurate than the non-distortion case above.

The present approach uses an improved model that considers all of the distortion to be floor distortion, and specifically models the floor eddy currents instead of just adding the P vector used in the '745 publication. In the present approach, it is assumed that the eddy currents are caused by an image of the transmitter that is reflected across the floor plane, i.e., an imaginary transmitter that appears as if it is under the floor by the same distance as the height of the actual transmitter.

Figure 2:
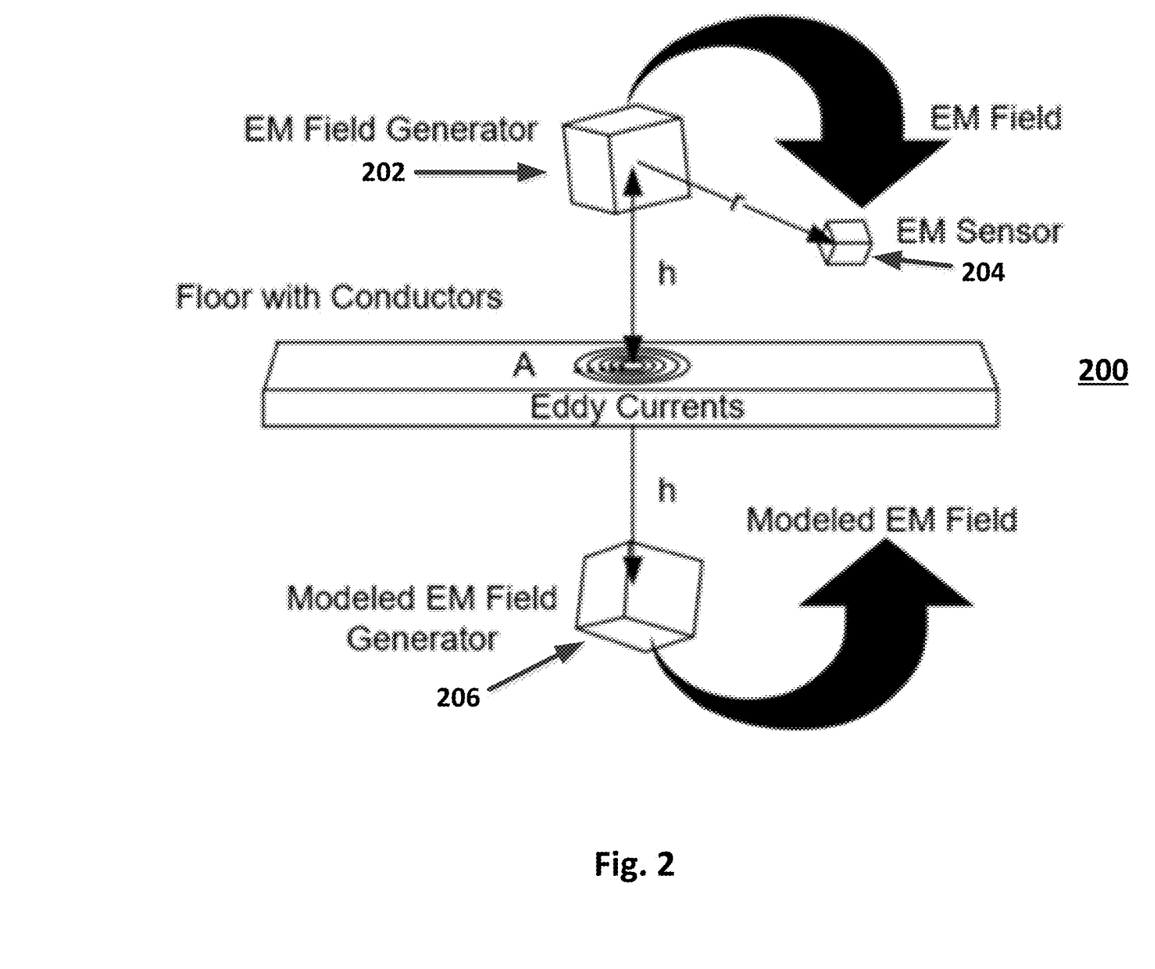
FIG. 2 is a diagram illustrating the modeling of distortion of the magnetic field in one embodiment of the present approach.

FIG. 2 illustrates this model of the present approach. A system 200 contains a magnetic field transmitter 202 located at a height h above a floor, and a magnetic sensor, or receiver, 204. A second, modeled magnetic field transmitter 206 that is assumed to cause the eddy currents in the floor is reflected along the z-axis, i.e., located at a second location that is a distance h below the floor.

Limiting the source of the eddy currents to such a theoretical second transmitter in this model results in a different equation than Equation 3 of the '745 publication. Now, the SigMat is given by:

$$X(r, y, h, A) = R(y)'\left[B(r) + B(r + 2h\hat{k})\begin{vmatrix} 1 & 0 & 0 \\ 0 & 1 & 0 \\ 0 & 0 & -1 \end{vmatrix} A \right] * R_{tx} \quad \text{(Equation 4)}$$

where:
- B(r) again constitutes the primary SigMat;

$$B(r + 2h\hat{k})\begin{vmatrix} 1 & 0 & 0 \\ 0 & 1 & 0 \\ 0 & 0 & -1 \end{vmatrix}$$

describes the SigMat portion due to the eddy currents expected of an image of the transmitter reflected across the floor plane. As above, h is the height of the transmitter above the floor, so that the reflected image appears at a position a distance h below the floor as shown in FIG. 2;
- R(y) is again the rotation matrix as defined by the constant sensor IMU pitch and roll and the given yaw parameter y;
- $R_{tx}$ is again the rotation matrix obtained from the transmitter IMU;
- A is the gain (or attenuation) of the reflected image, which can be impacted by the amount and type of conductive material in the floor;
- $\hat{k}$ is the unit vector along the Z axis, which is parallel to gravity with positive being towards the sky.

Figure 3:
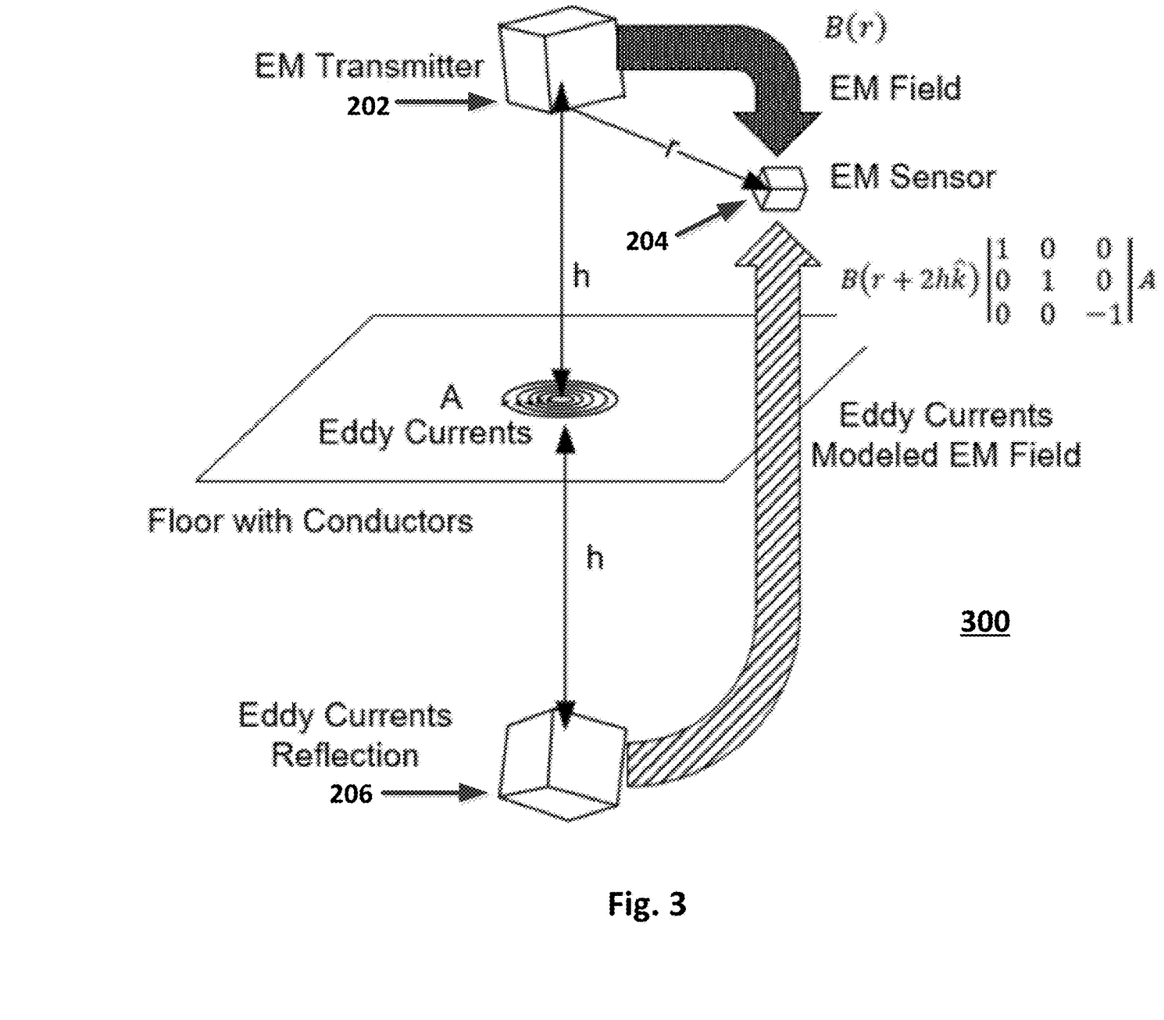
FIG. 3 is another diagram illustrating the modeling of distortion of the magnetic field in one embodiment of the present approach.

FIG. 3 further illustrates this model of the present approach, showing how the assumption of a second magnetic field is incorporated into Equation 4 above. System 300 contains the same components as system 200 of FIG. 2; the sensor 204 is now considered to effectively "detect" the superposition of two magnetic fields, one from transmitter 202 and another from the modeled transmitter 206. This approach adds two new dimensions to the parameter search space, rather than the three added in the approach of the '745 publication.

The optimization algorithm now attempts to find a value for X (r, θ, h, A) such that the equation (replacing X(x) in Equation 2 above):

$$F(r,\theta,h,A)=X_{meas}-X(r,\theta,h,A) \quad \text{(Equation 5)}$$

is again minimized.

One of skill in the art will appreciate that each proposed value of the position and orientation may be given an error value. This is done by comparing the SigMat derived from the sensed magnetic field at the receiver to a theoretical SigMat, taking into account the position and orientation of the receiver. By iterating the parameters in Equation 4 above so as to minimize the value of F (r, θ, h, A) in Equation 5 above, a more accurate position and orientation may be determined.

The techniques used to find the value of X (r, θ, h, A) that minimizes the value of F (r, θ, h, A) in Equation 5 above are similar to those used in the approach of the '745 publication. The Jacobian (as is known in the art, this refers to the Jacobian matrix and its determinant) of F (r, θ, h, A) is computed using numerical or analytic derivatives, and the Jacobian is used to compute a step that decreases the value of F. Iterations of this step are performed until a desired level of tolerance is achieved. For example, an algorithm such as the Levenberg-Marquardt algorithm, also known as the damped least-squares method, may be used.

In some embodiments, a determination is made as to whether the error between the measured SigMat and a theoretical SigMat is small enough for an intended purpose. The receiver senses the magnetic field in its local coordinate system, and a SigMat is determined from this; as above, this SigMat is denoted as $X_{meas}$. To evaluate the size of an error in the position and orientation of the receiver, possibly due to distortion, the SigMat corresponding to the theoretical dipole fields model at this solved position and orientation is calculated. The theoretic magnetic dipole field is computed at the receiver position (in transmitter coordinates), and then rotated according to the receiver's orientation to bring it into the receiver's local coordinate system. The resulting SigMat for the theoretical magnetic field is denoted here as $X_{PnO}$.

The error $E_x$ can then be calculated by:

$$E_X = \frac{\|X_{PnO} - X_{meas}\|}{\|X_{meas}\|} \quad \text{(Equation 6)}$$

This is a dimensionless quantity that reflects the proportion of unexplained measured SigMat compared to the theoretical model (the recomputed SigMat).

If, for example, the computed $E_x$ is greater than 20%, this indicates that at least 20% of the measured SigMat is not explained by the recomputed SigMat, thus indicating that there is some type of magnetic distortion or interference present.

Now suppose the floor-distortion optimization approach above is used (by minimizing Equation 5), and a new position and orientation is determined, which will be different. The distortion-subtracted SigMat (according to the physical model) at the new position and orientation is computed, and the error $E_x$ is again computed.

If $E_x$ is, for example, now 3%, this means that 97% of the measured SigMat is explained by the recomputed SigMat, which indicates that most of the distortion was coming from the floor (and/or ceiling). On the other hand, if $E_x$ is still over 20% then there is still some unknown distortion from a source other than the floor.

If the distortion in a magnetic tracking system is primarily or entirely due to floor distortion, the iterative process will result in a convergence of the value of F (r, θ, h, A) in Equation 5 above at a point at which it is at a minimum. In various embodiments, the optimization may run until this point is reached, i.e., the value of F (r, θ, h, A) converges at a minimum. In other embodiments, the iterative process may run until the size of the error $E_x$ reaches a sufficiently small desired value, or until some predetermined time period or a selected number of iterations have occurred.

In some situations, the value of F (r, θ, h, A) may not converge. In other situations, the value of $E_x$ may remain at an undesirably high level due to other distortion, as mentioned above. In either of these situations, it may be appropriate to acknowledge that the distortion cannot be removed by the present approach and that the resulting position and orientation may be, and likely is, inaccurate. In that case, the process may be run again, or other error correction methods such as those discussed above may be implemented. If the error is too great and cannot be corrected, the transmitter and receiver may not synchronize, or, if previously synchronized, may desynchronize.

The present approach improves the correction for floor distortion compared to the approach of the '745 publication. To assess the performance of the respective error correction methods, a comparative accuracy test of a magnetic tracking system with the different error correction methods was conducted. Sensors were placed in locations corresponding to approximately where a user's foot and knee would be located (on the basis that other sensors on a user's body would be farther from the floor and therefore less affected by floor distortion), and in different distortion conditions:

(a) High distortion—a 1 meter×1 meter sheet metal plate located under the sensors;
(b) Typical distortion—on the floor of an industrial building;
(c) Low distortion—the test setup 1.5 meters above the floor, or outside a building.

Table 1 below shows the measured amounts of error in the position of the sensors in each distortion setting, and with no distortion correction, correction using the approach of the '745 publication, or the present approach.

TABLE 1

Comparative Accuracy Test Results

| | (a) High Distortion | | (b) Typical Distortion | | (c) Low Distortion | |
| --- | --- | --- | --- | --- | --- | --- |
| | Foot Sensor | Knee Sensor | Foot Sensor | Knee Sensor | Foot Sensor | Knee Sensor |
| No Distortion Correction Error [mm] | >200 | 94 | >200 | 77 | 7 | 7 |
| '745 publication approach Error [mm] | 129 | 20 | 62 | 4 | 6 | 10 |
| Present approach Error [mm] | 45 | 8 | 26 | 4 | 17 | 7 |

As seen in Table 1 above, in the high distortion case there is a significant improvement of accuracy for the foot sensor using the present approach, with no distortion correction having an error of more than 200 mm, the '745 publication approach having an error of 129 mm and the present approach having only a 45 mm error. Similarly, in the typical distortion case, the present approach has significantly better results than the other methods. In the low distortion case, the present approach has slightly worse results, but the results are still at what will probably be considered to be an acceptably low level for most applications. In the case of the knee sensor, as also shown by the results in Table 1, the present approach is as good as or better than the other approaches in all cases.

This improved accuracy is particularly useful in applications where precise determination of the position and orientation of a user's foot and knee is important. For example, where the user is a patient undergoing physical or occupational therapy in a virtual reality environment, this greater accuracy can be particularly relevant to determining their actual therapeutic progress.

Figure 4:
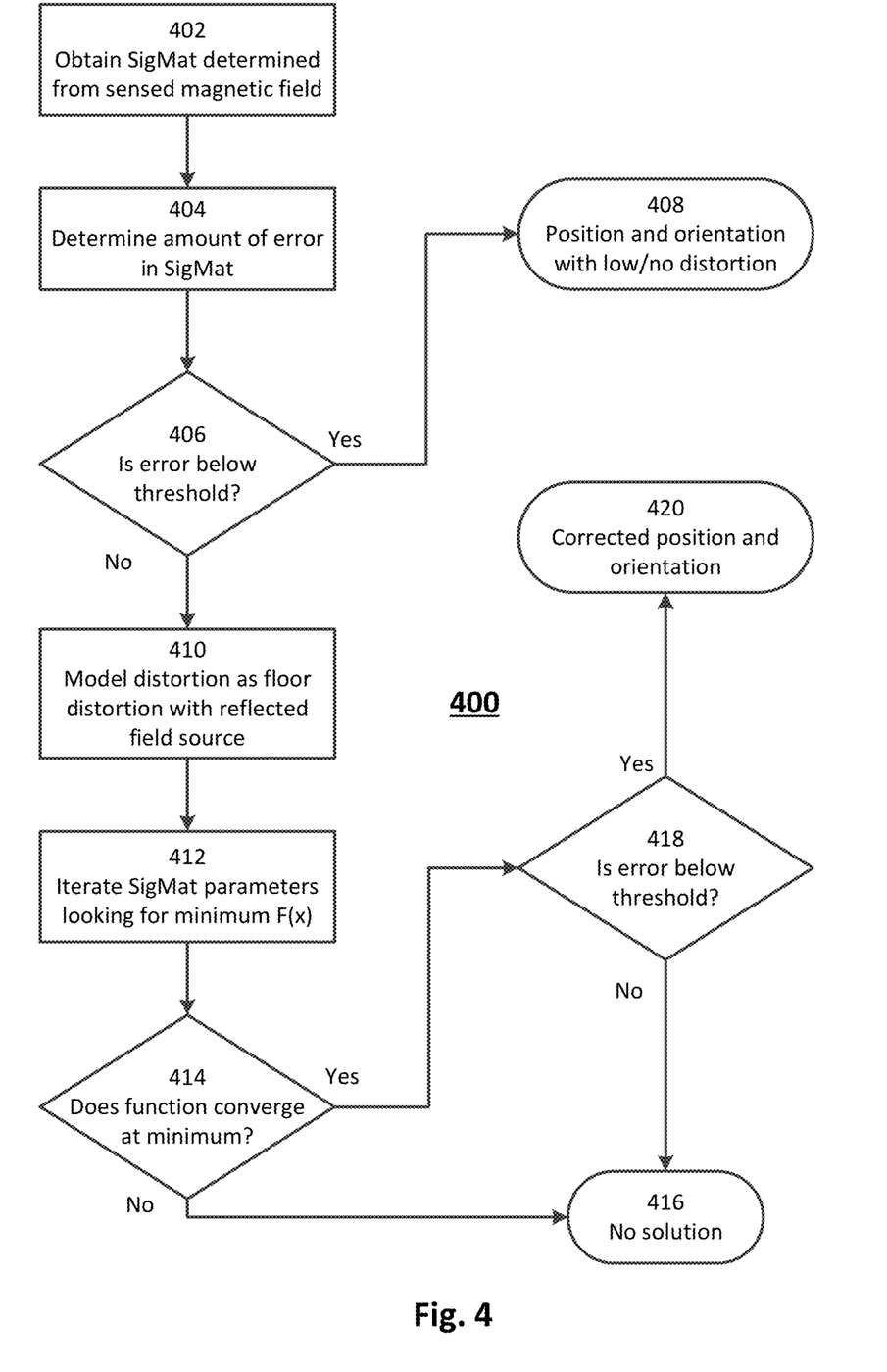
FIG. 4 is a flowchart of a process for reducing magnetic tracking error due to distortion of the magnetic field in a magnetic tracking system according to one embodiment of the present approach.

FIG. 4 is a flowchart of a process 400 for reducing magnetic tracking error due to distortion of the magnetic field in a magnetic tracking system according to one embodiment of the present approach. At step 402, a processor, such as processor 106 in FIG. 1, obtains a SigMat that has been determined from the sensed magnetic field, using data from the sensing coils in a receiver, such as sensing coils 112 in receiver 104 in FIG. 1. In some embodiments, the processor itself determines the SigMat from the data, while in alternative embodiments, the processor may receive a SigMat that has already been determined from such data by, for example, a processor in the receiver.

At step 404, the processor detects whether the amount of any error in the value of SigMat due to electromagnetic distortion, for example by using a calculation such as that in Equation 6 above.

At step 406, the processor determines whether any error in the value of SigMat is below a predetermined threshold. If the error is below the threshold, at step 408 the position and orientation of the receiver is determined and considered to have low or no distortion.

If the error is over the threshold, at step 410 the processor models the distortion as floor distortion, for example, using the approach described above with respect to Equation 4. At step 412 the processor then iterates the parameters of SigMat, such as those in Equation 4, seeking a minimum of the function F(x), in this case F (r, θ, h, A) as in Equation 5 above. As above, the iteration in step 412 may continue until the function F(x) has converged, or until some number of iterations have occurred or some predetermined amount of time has passed.

At step 414 the processor determines whether the function F(x) has converged. If the function does not converge, in some embodiments the processor may indicate at step 416 that there is no solution; in other embodiments, the process may start over, and only arrive at step 416 after some predetermined number of attempts to minimize the function.

If the function has converged, at step 418 the processor determines whether the error, again, for example, calculated as in Equation 6 above, is now below the predetermined threshold. If the error is below the threshold, the processor determines the corrected position and orientation of the receiver at step 420, for example, by determining the parameter vector that minimizes Equation 5 above. If, however, the error is still not below the threshold, the processor may again indicate at step 416 that there is no solution for the receiver's position and orientation and may desynchronize the receiver from the transmitter.

One of skill in the art will appreciate that these steps may be implemented in slightly different ways, for example, with respect to the specific order of some steps, what thresholds are provided, when the processor should indicate a lack of solution, etc. It will also be appreciated that it is expected that the steps of process 400 will generally run continuously many times per second when a magnetic tracking system is used with the present approach, and that faster processors will result in more corrections per second, and thus a more accurate real-time indication of the position and orientation of a receiver.

It will be appreciated by one of skill in the art that the predetermined threshold at which the error of SigMat is considered too great may be set at a desired value by a designer, and that certain factors are likely to influence that decision. If the threshold is too low, a system using the present method will aggressively reject SigMat solutions and find many instances of desynchronization as described above. On the other hand, if the threshold is too high, the system will be too tolerant of noise and confounding magnetic fields, leading to instances in which the receiver is desynchronized but the system is unable to detect it.

Some experiments have evaluated the maximum SigMat error in typical use cases around distorted magnetic fields, and suggest that a reasonable threshold is a 30% error, i.e., that such a threshold will make sure that the receiver remains synchronized while still producing reasonably good results. One of skill in the art will be able to determine whether a different threshold is appropriate for a particular use case, and will appreciate the various system parameters that may be adjusted to achieve any desired threshold.

The disclosed system and method has been explained above with reference to several embodiments. Other embodiments will be apparent to those skilled in the art in light of this disclosure. Certain aspects of the described method and apparatus may readily be implemented using configurations or steps other than those described in the embodiments above, or in conjunction with elements other than or in addition to those described above. It will also be apparent that in some instances the order of steps described herein may be altered without changing the result of performance of all of the described steps.

There may be a single processor, or multiple processors performing different functions of the functions described herein. One of skill in the art will appreciate how to determine which and how many processors will be appropriate for a specific intended application, and where in a given system they might be located. In some embodiments a single processor may perform all of the processing functions described herein; in other embodiments, the receiver may contain a separate processor to compute the SigMat from the sensor data.

It should also be appreciated that the described method and apparatus can be implemented in numerous ways, including as a process, an apparatus, or a system. The methods described herein may be implemented by program instructions for instructing a processor to perform such methods, and such instructions recorded on a non-transitory computer readable storage medium such as a hard disk drive, floppy disk, optical disc such as a compact disc (CD) or digital versatile disc (DVD), flash memory, etc. It may be possible to incorporate the described methods into hard-wired logic if desired. It should be noted that the order of the steps of the methods described herein may be altered and still be within the scope of the disclosure.

These and other variations upon the embodiments are intended to be covered by the present disclosure, which is limited only by the appended claims.

What is claimed is:

1. A system for reducing magnetic tracking error in a determined position and orientation of a receiver in an electromagnetic tracking system, comprising:
   a transmitter positioned at a height above a floor and having a plurality of source magnetic coils configured to generate a magnetic field;
   a receiver having a plurality of sensor magnetic coils configured to sense the magnetic field and generate magnetic sensor data; and
   a processor configured to:
      determine that there is error due to distortion of the magnetic field in the determined position and orientation of the receiver relative to the transmitter as represented by a first signal matrix created using the magnetic sensor data from the sensor magnetic coils;
      determine that the error due to distortion of the magnetic field in the determined position and orientation of the receiver represented by the first signal matrix exceeds a predetermined threshold;
      model the distortion of the magnetic field as a result of eddy currents in the floor, wherein the eddy currents are modeled as being caused by an imaginary transmitter positioned at a distance below the floor equal to the height of the transmitter;
      determine from the model of the distortion of the magnetic field a correction factor to compensate for the error in the position and orientation of the receiver represented by the first signal matrix;
      compute a second signal matrix by applying the first correction factor to the first signal matrix; and
      determine a corrected position and orientation of the receiver from the second signal matrix.

2. The system of claim 1 wherein the processor, configured to model the distortion of the magnetic field as a result of eddy currents in the floor under the transmitter, is further configured to model the distortion of the magnetic field as a result of eddy currents as being caused by a reflection of the transmitter along a vertical axis relative to the floor.

3. The system of claim 1 wherein the processor is further configured to determine the correction factor with an algorithm that iterates variables of the first signal matrix to find a minimum value of a difference function between the first signal matrix and a second signal matrix that is expected from a given position and orientation.

4. The system of claim 1 wherein the processor is further configured to iterate the variables of the signal matrix by taking a Jacobian matrix of the difference function and iterating with a damped least-squares method.

5. A method of reducing magnetic tracking error in a determined position and orientation of a receiver in an electromagnetic tracking system, comprising:
   generating a magnetic field from a plurality of source magnetic coils in a transmitter, wherein the transmitter is positioned at a height above a floor;
   generating magnetic sensor data by sensing the magnetic field using a plurality of sensor magnetic coils in a receiver; and
   determining, by a processor, that there is error due to distortion of the magnetic field in the determined position and orientation of the receiver relative to the transmitter as represented by a first signal matrix created using the magnetic sensor data from the sensor magnetic coils;
   determining, by the processor, that the error due to distortion in the magnetic field in the determined position and orientation of the receiver represented by the first signal matrix exceeds a predetermined threshold;
   modeling, by the processor, the distortion of the magnetic field as a result of eddy currents in the floor, wherein the eddy currents are modeled as being caused by an imaginary transmitter positioned at a distance below the floor equal to the height of the transmitter;
   determining, by the processor, from the model of the distortion of the magnetic field a correction factor to compensate for the error in the position and orientation of the receiver represented by the first signal matrix; and
   computing, by the processor, a second signal matrix by applying the first correction factor to the first signal matrix; and
   determining, by the processor, a corrected position and orientation of the receiver from the second signal matrix.

6. The method of claim 5 wherein modeling, by the processor, of the distortion as a result of eddy currents in the floor further comprises modeling the eddy currents as being caused by a reflection of the transmitter along a vertical axis.

7. The method of claim 5 further comprising determining, by the processor, the correction factor with an algorithm that iterates variables of the first signal matrix to find a minimum value of a difference function between the first signal matrix and a second signal matrix that is expected from a given position and orientation.

8. The method of claim 5 further comprising, iterating, by the processor, the variables of the signal matrix by taking a Jacobian matrix of the difference function and iterating with a damped least-squares method.

9. A non-transitory computer readable storage medium having embodied thereon instructions for causing a computing device to execute a method of reducing magnetic tracking error in a determined position and orientation of a receiver in an electromagnetic tracking system, the method comprising:
   generating a magnetic field from a plurality of source magnetic coils in a transmitter, wherein the transmitter is positioned at a height above a floor;
   generating magnetic sensor data by sensing the magnetic field using a plurality of sensor magnetic coils in a receiver; and
   determining, by a processor, that there is error due to distortion of the magnetic field in the determined position and orientation of the receiver relative to the transmitter as represented by a first signal matrix created using the magnetic sensor data from the sensor magnetic coils;
   determining, by the processor, that the error due to distortion of the magnetic field in the determined position and orientation of the receiver represented by the first signal matrix exceeds a predetermined threshold;
   modeling, by the processor, the distortion of the magnetic field as a result of eddy currents in the floor, wherein the eddy currents are modeled as being caused by an imaginary transmitter positioned at a distance below the floor equal to the height of the transmitter;
   determining, by the processor, from the model of the distortion of the magnetic field a correction factor to compensate for the error in the position and orientation of the receiver represented by the first signal matrix; and
   computing, by the processor, a second signal matrix by applying the first correction factor to the first signal matrix; and
   determining, by the processor, a corrected position and orientation of the receiver from the second signal matrix;
   run in real-time with no additional hardware or calibration required.

* * * * *